（12）United States Patent
Aldrich et al.

(10) Patent No.: US 8,021,375 B2
(45) Date of Patent: Sep. 20, 2011

(54) SURGICAL CLIP APPLICATOR

(75) Inventors: George Aldrich, Clinton, NY (US);
Stephen M. Green, Syracuse, NY (US);
Mike Bennett, Charlestown, NH (US)

(73) Assignee: ConMed Corporation, Utica, NY (US)

( * ) Notice: Subject to any disclaimer, the term of this patent is extended or adjusted under 35 U.S.C. 154(b) by 821 days.

(21) Appl. No.: 12/106,749

(22) Filed: Apr. 21, 2008

(65) Prior Publication Data

US 2009/0264904 A1    Oct. 22, 2009

(51) Int. Cl.
*A61B 17/10* (2006.01)
(52) U.S. Cl. ......................................... 606/143
(58) Field of Classification Search .......... 606/142–143, 606/213; 623/23.72
See application file for complete search history.

(56) References Cited

U.S. PATENT DOCUMENTS

| | | | |
|---|---|---|---|
| 3,740,994 A | 6/1973 | DeCarlo, Jr. | |
| 4,802,614 A | 2/1989 | Green et al. | |
| 4,821,942 A | 4/1989 | Richards et al. | |
| 5,258,010 A | 11/1993 | Green et al. | |
| 5,344,061 A | 9/1994 | Crainich | |
| 5,487,499 A | 1/1996 | Sorrentino et al. | |
| 5,564,615 A | 10/1996 | Bishop et al. | |
| 5,588,581 A | 12/1996 | Conlon et al. | |
| 5,601,224 A | 2/1997 | Bishop et al. | |
| 5,607,436 A | 3/1997 | Pratt et al. | |
| 5,615,820 A | 4/1997 | Viola | |
| 5,634,584 A | 6/1997 | Okorocha et al. | |
| 5,662,662 A | 9/1997 | Bishop et al. | |
| 5,715,988 A | 2/1998 | Palmer | |
| 5,718,359 A | 2/1998 | Palmer et al. | |
| 5,762,255 A | 6/1998 | Chrisman et al. | |
| 5,772,673 A | 6/1998 | Cuny et al. | |
| 5,792,150 A | 8/1998 | Pratt et al. | |
| 5,839,639 A | 11/1998 | Sauer et al. | |
| 6,155,473 A | 12/2000 | Tompkins | |
| 6,277,131 B1 * | 8/2001 | Kalikow | 606/143 |
| 6,569,171 B2 | 5/2003 | DeGullebon et al. | |
| 6,817,508 B1 | 11/2004 | Racenet et al. | |
| 6,817,509 B2 | 11/2004 | Geiste et al. | |
| 6,866,178 B2 | 3/2005 | Adams et al. | |
| 6,874,669 B2 | 4/2005 | Adams et al. | |
| 6,911,033 B2 | 6/2005 | de Guillebon et al. | |
| 7,048,171 B2 | 5/2006 | Thornton et al. | |
| 2006/0058818 A1 | 3/2006 | Liberatore et al. | |
| 2006/0081678 A1 | 4/2006 | Ehrenfels et al. | |
| 2006/0151569 A1 | 7/2006 | Ehrenfels et al. | |

* cited by examiner

*Primary Examiner* — Melanie Tyson
*Assistant Examiner* — Son Dang
(74) *Attorney, Agent, or Firm* — Timothy D Evans (57) ABSTRACT

A surgical clip applicator for applying surgical clips to body tissue includes an elongated ram housing that has proximal and distal ends and at least partially encloses a ram. A trigger housing includes a trigger that has an open position and a closed position. The trigger housing is mounted to the proximal end of the ram housing. The ram extends partially into the trigger housing and is operatively connected to the trigger. The trigger is spaced a first distance from the trigger housing in the open position and spaced a second distance from the trigger housing in the closed position. The first distance being larger than the second distance. A cartridge is removably mounted into the ram housing. The cartridge includes a plurality of the surgical clips. A retaining mechanism retains the trigger with respect to the trigger housing between the open and closed positions. Mounting the cartridge into the distal end of the ram housing urges at least a portion of the ram into the housing to set the trigger in the open position.

20 Claims, 7 Drawing Sheets

SURGICAL CLIP APPLICATOR

BACKGROUND OF THE INVENTION

This invention generally relates to a surgical clip applicator and, more particularly, to a surgical clip applicator having a replaceable cartridge for storing and applying a plurality of clips.

Clip applicators, or surgical staplers, for clipping or stapling clips within a human body are known. In laparoscopic and endoscopic surgical procedures, a small incision is made in the patient's body to provide access for a tube or working channel. Once extended into the patient's body, the working channel provides an access port which allows insertion of various surgical instruments through the working channel for accessing organs, blood vessels, ducts or body tissue spaced inwardly from the incision. Often during such procedures, it is necessary to use a clip applicator to apply clips to blood vessels or various ducts or other body tissue for various reasons including to prevent the flow of body fluids therethrough during the procedure and/or to hold stunts, catheters and other devices in place.

Clip applicators are known to include an elongated, narrow housing and a disposable cartridge releasably mounted to the distal end of the housing. The disposable cartridge includes a plurality of clips and a pair of jaws that extend from the distal end of the cartridge. During use, the cartridge and part of the housing are inserted through the working channel and into the body. Once the jaws are positioned around the desired tissue and/or device, the surgeon squeezes a trigger located outside of the body to activate a clip driver within the cartridge that advances one of the clips to a position between the jaws. Further squeezing of the trigger squeezes the jaws together to pinch the clip onto the body tissue and/or device. The clip may be partially closed in certain applications, such when used to hold a catheter in or shunt in place, or the clip may be nearly completely pinched together. The trigger preferably includes a ratchet such that the surgeon can pause during installation of the clip without prematurely releasing the jaws and losing the partially closed clip held between the jaws. Once the trigger has been fully compressed or compressed a predetermined distance, the ratchet is released and jaws are opened to release the clip. The clip applicator is then ready to install another clip if needed. Once all of the clips in the cartridge have been used, or the cartridge needs to be otherwise replaced, the cartridge is removed and disposed of and a new cartridge is installed onto the end of the clip applicator. If the trigger is accidentally squeezed or the trigger is otherwise displaced during replacement of the cartridge from a fully open position, the second cartridge will not properly align with the driving members in the housing requiring the surgeon to manually reset the trigger and then remount the cartridge.

The cartridge has a clip driver for advancing the clips and a jaw driver for closing the jaws. Because the clip and jaw drivers must align with the corresponding driving members in the clip applicator housing, it is important that the clip and jaw drivers are properly aligned and held in place until the cartridge is fully installed and the first and second driving members are properly connected with the driving members of the housing. Any displacement of the clip and jaw drivers will prevent proper alignment between the driving members and prevent the clip applicator from working.

What is therefore needed, but not provided in the prior art, is a trigger release mechanism for a surgical clip applicator that automatically releases a retaining member and automatically resets the trigger to a fully open position in response to loading of a new cartridge and a cartridge for a surgical clip applicator that has a releasable alignment member for keeping the driving members of the cartridge properly aligned until the cartridge is completely loaded within the clip applicator housing.

BRIEF SUMMARY OF THE INVENTION

Briefly stated, the present invention is directed to a surgical clip applicator for the application of a surgical clip within the human body. The surgical clip applicator includes a ram housing that has proximal and distal ends and at least partially encloses a ram. A trigger housing includes a trigger that has an open position and a closed position. The trigger housing is mounted to the proximal end of the ram housing. The ram extends partially into the trigger housing and is operatively connected to the trigger. A retaining mechanism retains the trigger with respect to the trigger housing between the open and closed positions. The trigger is spaced a first distance from the trigger housing in the open position and is spaced a second distance from the trigger housing in the closed position. The first distance is larger than the second distance. A cartridge is removably mounted into the distal end of the ram housing. The cartridge includes a plurality of surgical clips. Mounting the cartridge into the distal end of the ram housing urges at least a portion of the ram into the trigger housing to set the trigger in the open position.

In another aspect, the invention is directed to a surgical clip applicator for the application of a surgical clip to body tissue. The surgical clip applicator comprises an elongated ram housing that has proximal and distal ends and at least partially encloses a ram. A trigger housing includes a trigger that has an open position and a closed position. The trigger housing is mounted to the proximal end of the ram housing. The ram extends partially into the trigger housing and is operatively connected to the trigger. The trigger is spaced a first distance from the trigger housing in the open position and is spaced a second distance from the trigger housing in the closed position. The first distance is larger than the second distance. The trigger urges the ram toward the distal end of the ram housing as the trigger is moved from the open position to the closed position. A cartridge is removably mounted into the distal end of the ram housing. The cartridge includes a plurality of surgical clips and a pair of opposed jaws that extend from a distal end of the cartridge. A clip driver advances one of the plurality of surgical clips at a time into the jaws when urged toward the distal end of the cartridge by the ram. A jaw driver closes the jaws to pinch the one surgical clip when the jaw driver is urged toward the distal end of the cartridge by the ram. A retaining mechanism retains the trigger with respect to the trigger housing between the open and closed positions. Mounting the cartridge to the distal end of the ram housing urges at least a portion of the ram into the housing to set the trigger in the open position.

In another aspect, the invention is directed to a surgical clip cartridge for use with a surgical clip applicator for the application of a surgical clip to body tissue. The surgical clip applicator has an elongated ram housing that has proximal and distal ends and includes a ram. A trigger housing is mounted to the proximal end of the ram housing. The ram extends partially into the trigger housing and is operatively connected to a trigger that has an open position and a closed position. The trigger is spaced a first distance from the trigger housing in the open position and is spaced a second distance from the trigger housing in the closed position. The first distance is larger than the second distance. The trigger urges the ram toward the distal end of the ram housing as the trigger is moved from the open position in which the trigger is enabled to initiate the application of a clip, to the closed position in which the clip has been applied. The cartridge is removably mounted into the distal end of the ram housing. The cartridge includes a cartridge housing and a plurality of surgical clips. A pair of opposed jaws extends from a distal end of the cartridge housing. A clip driver disposed within the cartridge housing is provided for advancing one of the plurality of surgical clips at a time into the jaws when urged by the ram. A jaw driver is disposed within the cartridge housing for closing the jaws to pinch the one surgical clip when urged by the ram. An alignment member releasably retains the clip driver and the jaw driver in a mounted position such that the clip driver and the jaw driver are stationary with respect to each other and the cartridge housing releases the clip driver and jaw driver in an active position once the cartridge is mounted into the ram housing and the trigger is moved out of the open position.

BRIEF DESCRIPTION OF THE SEVERAL VIEWS OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown.

In the drawings.

DETAILED DESCRIPTION OF THE INVENTION

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of a surgical clip applicator in accordance with the present invention, and designated parts thereof. Unless specifically set forth herein, the terms "a", "an" and "the" are not limited to one element but instead should be read as meaning "at least one". The terminology includes the words noted above, derivatives thereof and words of similar import.

Referring to the drawings in detail, wherein like reference numerals indicate like elements throughout, there is shown in FIGS. 1-4D a preferred embodiment of a surgical clip applicator, generally designated 10, in accordance with the present invention. The surgical clip applicator 10 is preferably used to apply (one at a time) a plurality of surgical staples or clips ("clips") 12 (FIG. 2) within a human body (not shown). Specifically, the surgical clip applicator 10 is preferably used to apply clips 12 in endoscopic or other minimally invasive surgical procedures.

Figure 1:
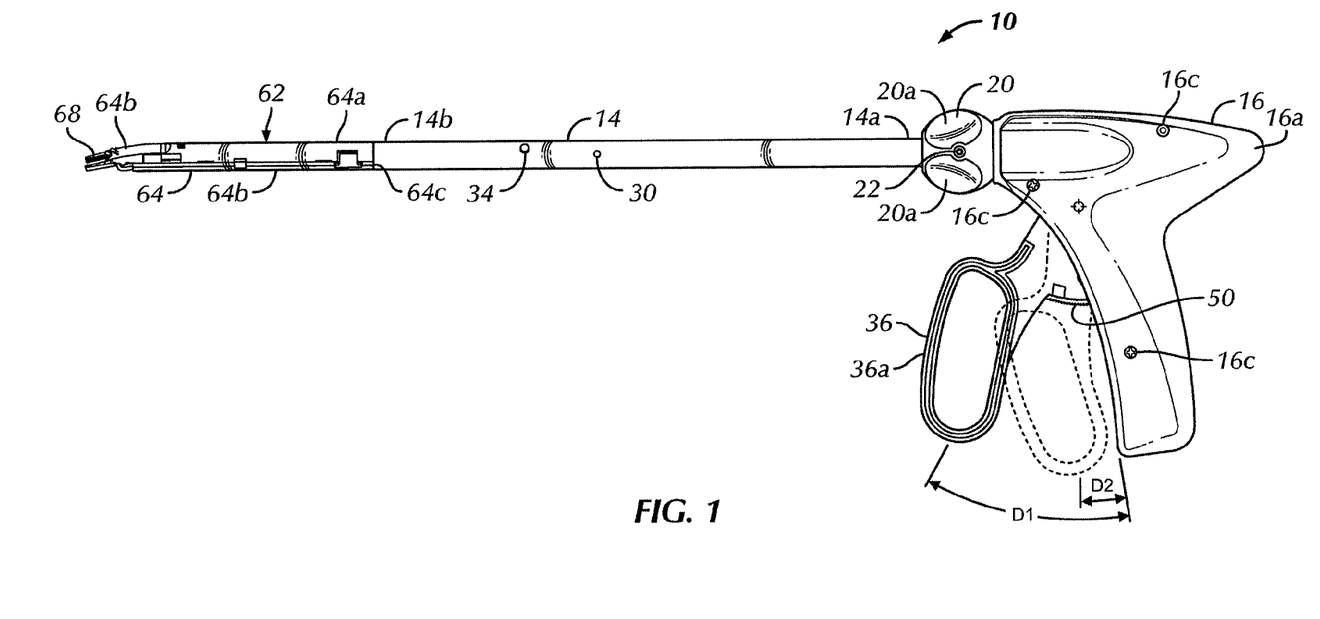
FIG. 1 side elevational view of a surgical clip applicator and cartridge in accordance with a preferred embodiment of the invention in a fully assembled position.

Referring to FIG. 1, the surgical clip applicator 10 includes an elongated ram housing 14 that has a proximal end 14a and a distal end 14b. The ram housing 14 is preferably a generally hollow cylindrical tube and is preferably constructed of a rigid lightweight material such as stainless steel. However, the ram housing 14 may have any shape such as triangular or rectangular and may be constructed of any suitable material such as aluminum or a polymeric material. The proximal end 14a of the ram housing 14 is mounted to a trigger housing 16. The ram housing 14 is preferably rotatably mounted to the trigger housing 16 and includes a ratchet gear 18 (FIG. 4A) that is engagement with a pawl (not shown) such that the ram housing 14 is incrementally rotated by a predetermined amount of force and does not freely rotate relative to the trigger housing 16. The ram housing 14 may be fixably attached to the trigger housing 16 or the ram housing 14 and/or trigger housing 16 may include a lock (not shown) to fix the ram housing 14 in place once the ram housing 14 has been rotated with respect to the trigger housing 16 to the desired position.

Figure 3:
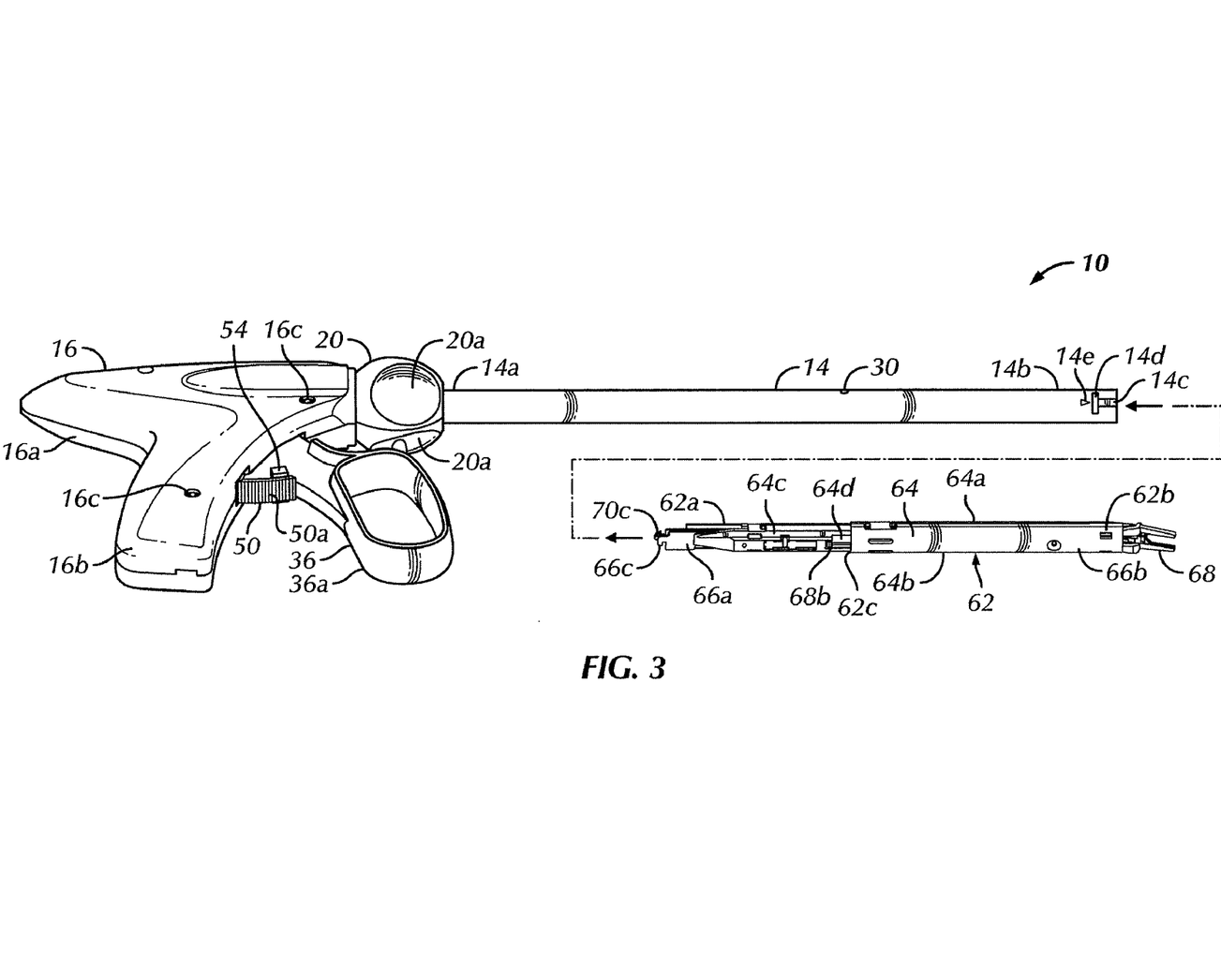
FIG. 3 is a bottom perspective view of the surgical clip applicator and cartridge in an unassembled position and demonstrating the position of the cartridge relative to the surgical clip applicator for mounting the cartridge to the surgical clip applicator.

Referring to FIG. 3, the distal end 14b of the ram housing 14 preferably includes an inwardly extending projection 14c preferably having a v-shape. However the projection 14c may have any shape or may alternatively be a groove to accept a projection (not shown). The distal end 14b of the ram housing 14 also preferably includes a rectangular shaped opening 14d that extends through the ram housing 14 and an indicia 14e having an arrow shape. The proximal end 14a of the ram housing 14 preferably includes a grip 20 fixedly mounted to the ram housing 14 so that a surgeon or user (hereinafter referred to as "user") may better grip the ram housing 14 to rotate the ram housing 14 with respect to the trigger housing 16. The grip 20 preferably includes four equally spaced semi-spherical indents 20a such that an opposed thumb and index finger that may be wet with body fluid during use of the surgical clip applicator 10 are better received in the grip 20. The grip 20 is preferably constructed of a polymeric material such that the indents 20a are more easily formed, though the grip 20 may be constructed of any suitable material and have any shape. The grip 20 preferably includes a flush port 22 for flushing or cleaning the ram housing 14. The grip 20 is preferably sonically welded to the ram housing 14. However, the grip 20 may be secured to the ram housing 14 in any manner such as a compression or snap fit, the grip 20 may be integrally formed with the ram housing 14 or secured with epoxy or a fastener.

Figure 4A:
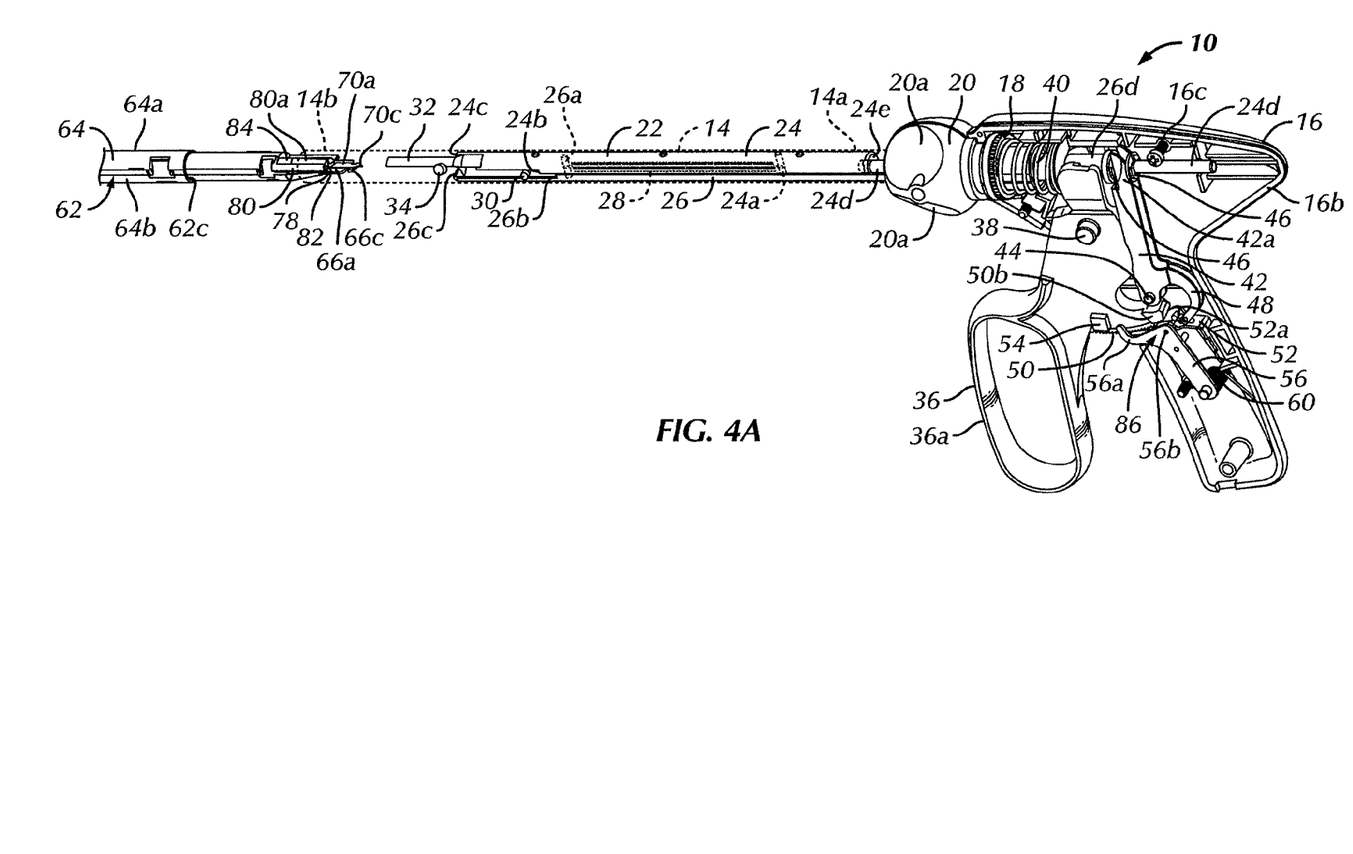
FIG. 4A is a perspective view of the surgical clip applicator and cartridge shown in FIG. 1 during initial mounting of the cartridge to the surgical clip applicator with a ram housing shown in phantom and a half of the trigger housing removed and a trigger of the surgical clip applicator in a partial closed or compressed position.

Referring to FIG. 4A, the ram housing 14 at least partially encloses a ram 22. The ram 22 is slideably disposed at least partially within the ram housing 14. The ram 22 preferably includes a clip ram 24 and a jaw ram 26. The clip ram 24 and the jaw ram 26 are preferably each in the form of a half cylinder but may be any other shape. The clip ram 24 is preferably independently slidable with respect to the jaw ram 26 and the clip ram 24 is preferably spring biased to the jaw ram 26 by a first spring member 28. The first spring member 28 is preferably a tension coil spring and is mounted to the clip ram 24 at a first spring mount 24a that extends from the clip ram 24 and is preferably mounted to the jaw ram 26 at a second spring mount 26a that extends from the jaw ram 26. Both the clip ram 24 and the jaw ram 26 preferably each include a pair of first and second edges 24b, 26b (only one side shown) respectively, that each circumferentially extend in opposing directions such that a gap is left between the clip ram 24 and jaw ram 26 toward the distal end of the ram 22. The first edge 24b of the clip ram 24 is preferably initially distal to the second edge 26b of the jaw ram 26 though the first edge 24b may be in any position relative to edge second 26b or only one of the clip ram 24 or jaw ram 26 may be indented or have a longitudinally extending groove (not shown). The ram housing 14 preferably includes a bar 30 that extends across the ram housing 14 between the clip ram 24 and jaw ram 26 and is distal to the first and second edges 24b, 26b. The bar 30 preferably prevents rotation of the ram 22 with respect to the ram housing 14. The bar 30 may be positioned anywhere along the ram 22 and may extend only partially across the ram housing 14 and have any shape such that the ram 22 engages with the ram 22 and prevents rotation of the ram 22 relative to the ram housing 14.

Figure 4B:
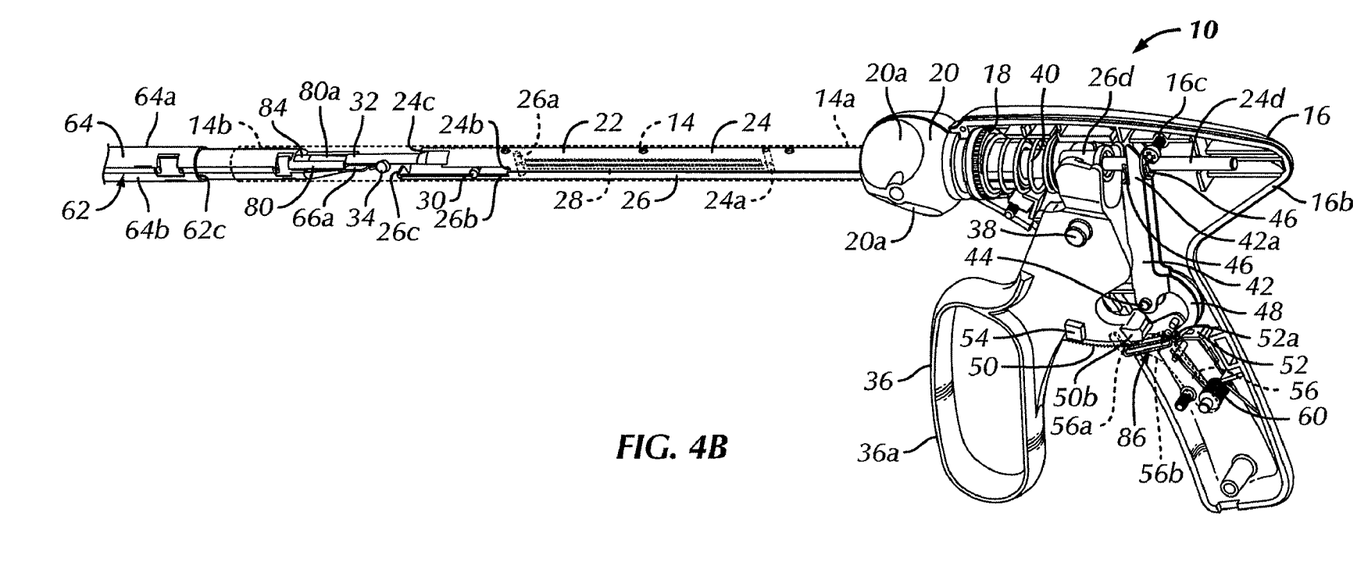
FIG. 4B is a perspective view of the surgical clip applicator and cartridge shown in FIG. 4A during mounting of the cartridge to the surgical clip applicator when the cartridge is engaged with a ram extension of the cartridge setting the trigger into an open position.
Figure 4C:
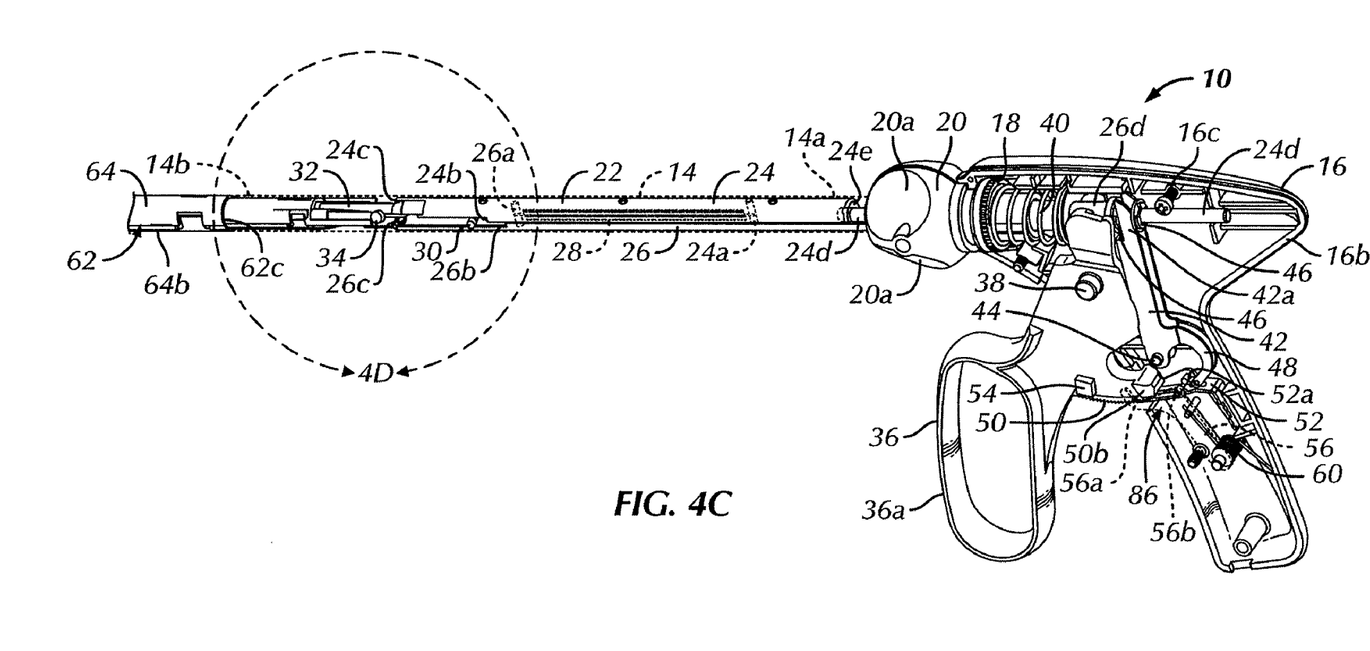
FIG. 4C is a perspective view of the surgical clip applicator and cartridge shown in FIG. 1 with a ram housing shown in phantom.
Figure 4D:
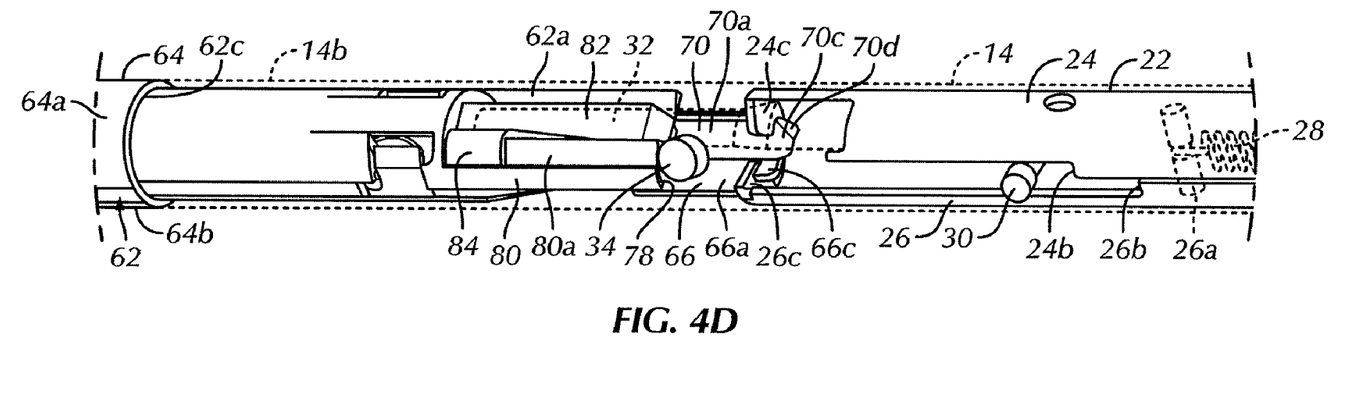
FIG. 4D is a partial, greatly enlarged, perspective view of the surgical clip applicator shown in FIG. 1 within area 4D in FIG. 4C.

Referring to FIGS. 4A and 4D, the distal end of the clip ram 24 includes an inwardly extending first catch 24c and the distal end of the jaw ram 26 includes an inwardly extending second catch 26c that is generally radially opposed from the first catch 24c. The first and second catches 24c, 26c are each preferably in the shape of a quarter circle in side view looking into the ram housing 14, but the first and second catches 24c, 26c may be any shape and are each preferably aligned at an angle, preferably 45 degrees from the bar 30.

The distal end of the clip ram 24 preferably includes a ram extension 32. The ram extension 32 preferably extends distally from the clip ram 24, is generally arcuate in shape and is flexible in the radial direction. The ram extension 32 is preferably welded to the clip ram 24. However, the ram extension 32 may have any shape and may be secured to the clip ram 24 in some other manner such as being integrally formed with the clip ram 24. The ram housing 14 preferably includes a ram support 34 that guides the ram extension 32 as the ram extension 32 slides distally and proximal with respect to the ram housing 14 and the ram support 34 slightly flexes the ram extension 32 radially inwardly to help keep the ram extension 32 properly aligned and connected.

The ram 22 extends partially into the trigger housing 16 such that the ram 22 extends through the grip 20. A proximal end 26d of the jaw ram 26 is preferably fully cylindrically shaped and positioned within the trigger housing 16. The proximal end 26d of the jaw ram 26 is preferably welded or otherwise fixedly connected to the jaw ram 26 though they may be integrally formed. The proximal end 26a of the jaw ram 26 is operatively connected to a trigger 36. The trigger 36 is pivotable with respect to the trigger housing 16 about a trigger axis 38. The trigger axis 38 is preferably integrally formed with the trigger 36 and extends into receiving divots (not shown) in the trigger housing 16. The trigger 36 has an opening to form a closed loop trigger handle 36a to facilitate movement in two directions. The trigger handle 36a may also have one or more open sides (not shown) and be formed in any shaped suitable to fit one or more fingers of a user's hand.

Referring to FIG. 1, the trigger 36 has an open position and closed position (the closed position shown in phantom). The trigger 36 is spaced a first distance D1 from the trigger housing 16 in the open position and the trigger 36 is spaced a second distance D2 from the trigger housing 16 in the closed position. The first distance D1 is substantially larger than the second distance D2.

Referring to FIG. 4A, the jaw ram 26 is spring biased from the trigger housing 16 by a second spring 40 within the trigger housing 16. The second spring 40 urges the jaw ram 26 back into the trigger housing 16 such that the trigger 36 is spring biased toward the open position. The clip ram 24 includes a rod 24d that extends from a point distal to the trigger housing 16 and through the jaw ram 26 and into the trigger housing 16. The clip ram 24 within the ram housing 14 is preferably connected to the rod 24d by a groove fitting 24e for manufacturing simplicity and to allow for assembly of the first spring member 28, but the clip ram 24 and the rod 24d may be fixedly attached. The clip ram 24 and the rod 24d may alternatively be integrally formed or molded if the clip ram 24 and rod 24d are constructed of a polymeric material. The cylindrical shape of the rod 24d allows the clip ram 24 to extend through and be slideable with respect to the proximal end 26d of the jaw ram 26 though the rod 24d may be any shape such as rectangular.

A ram pivot 42 is pivotably mounted within the trigger housing 16 proximal to the trigger 36 and pivotable about a ram pivot axis 44. The ram pivot 42 is operatively connected to the rod 24d and is movable with the rod 24d. A pair of snap rings 46 are preferably provided one on each side of the ram pivot 42 and are fixedly attached to the rod 24d. The snap rings 46 preferably each snap fit into a groove (not shown) on the rod 24d but the snap rings 46 may be fixedly attached to the rod 24d in any manner such as by being welded washers, or integrally formed. The ram pivot 42 is preferably has a split or forked-shaped end 42a such the rod 24d extends through the end 42a. Movement of the rod 42a proximally into the trigger housing 16 urges the end 42a proximally and pivots the ram pivot 42 about the ram pivot axis 44. Also, movement of the trigger 32 to urge the jaw ram 26 toward the distal end 14b of the ram housing 14 causes the trigger 32 to contact the ram pivot 42 and pivot the ram pivot 42 about the ram pivot axis 44 such that the rod 24d is urged proximally, the opposite direction of the jaw ram 26. The ram pivot 42 preferably includes a pivot extension 48 that is preferably arcuately shaped and extends below the ram pivot axis 44. Though the pivot extension 48 is preferably arcuately shaped to release the trigger 36 as described further below, the pivot extension 48 may be any shape. The ram pivot 42 and the pivot extension 48 are preferably integrally formed though the ram pivot 42 and the pivot extension 48 may be separately affixed or attached.

The trigger 36 preferably includes a retaining mechanism or member 86 for holding the trigger 36 stationary with respect to the trigger housing 16 and preferably includes a ratchet 50. The ratchet 50 preferably includes a plurality of equally spaced ratchet teeth 50a (see FIG. 3). The ratchet 50 is preferably convexly shaped to generally follow a constant length radius arc about the trigger axis 38 though the ratchet 50 may have any shape. The ratchet 50 extends from the trigger housing 16 in the open position and is positioned substantially within the trigger housing 16 in the closed position. A pair of laterally extending bosses 54 extend from the trigger 36 above the ratchet 50 and closest to the trigger handle 36a. A pawl 52 in the form of a leaf spring is preferably fixedly mounted within the trigger housing 16 but the pawl 52 may be any type of pawl and may be integrally formed with the trigger housing 16. The pawl 52 is spring biased into engagement with the ratchet 50 such that movement of the trigger 36 from the open position toward the closed position clicks the pawl 52 along the ratchet teeth 50a. The trigger 36 remains stationary when released because the pawl 52 engages with the ratchet teeth 50a and prevents the second spring 40 from pivoting the trigger 36 about the trigger axis 38 to return the trigger 36 to the open position. A toggle 56 is preferably provided within the trigger housing 16. The toggle 56 is pivotable about a toggle axis 58 and is spring biased by a third spring member 60, preferably in the form of a torsion coil spring, from the trigger housing 16 toward the trigger 36. The toggle 56 preferably includes a pair of arms 56a (only one side shown) that each extend alongside the ratchet 50. The pawl 52 preferably includes an upwardly extending catch or ridge 52a. The toggle 56 at least partially extends over the pawl 52 proximate the ridge 52a such that a portion of the toggle 56, such as a release bar 56b that extends across the toggle 56, may contact and disengage the pawl 52 from the ratchet 50 as described further below. The release bar 56b is shown to have a split configuration but the release bar 56b may extend continuously across the toggle 56.

Referring to FIGS. 1 and 3, the trigger housing 16 is preferably constructed of a polymeric material and is comprised of two complementary trigger housing halves 16a, 16b that are held together by a snap fitting and a plurality of screws 16c. However, the trigger housing 16 may be constructed of any material such as metal and may be held together by any fastener and/or connection configuration and may be releasably or unreleasably attached to each other. The trigger housing 16 may have any shape that is suitable for covering the various components and for fitting or contouring to the shape of the user's hand.

Figure 2:
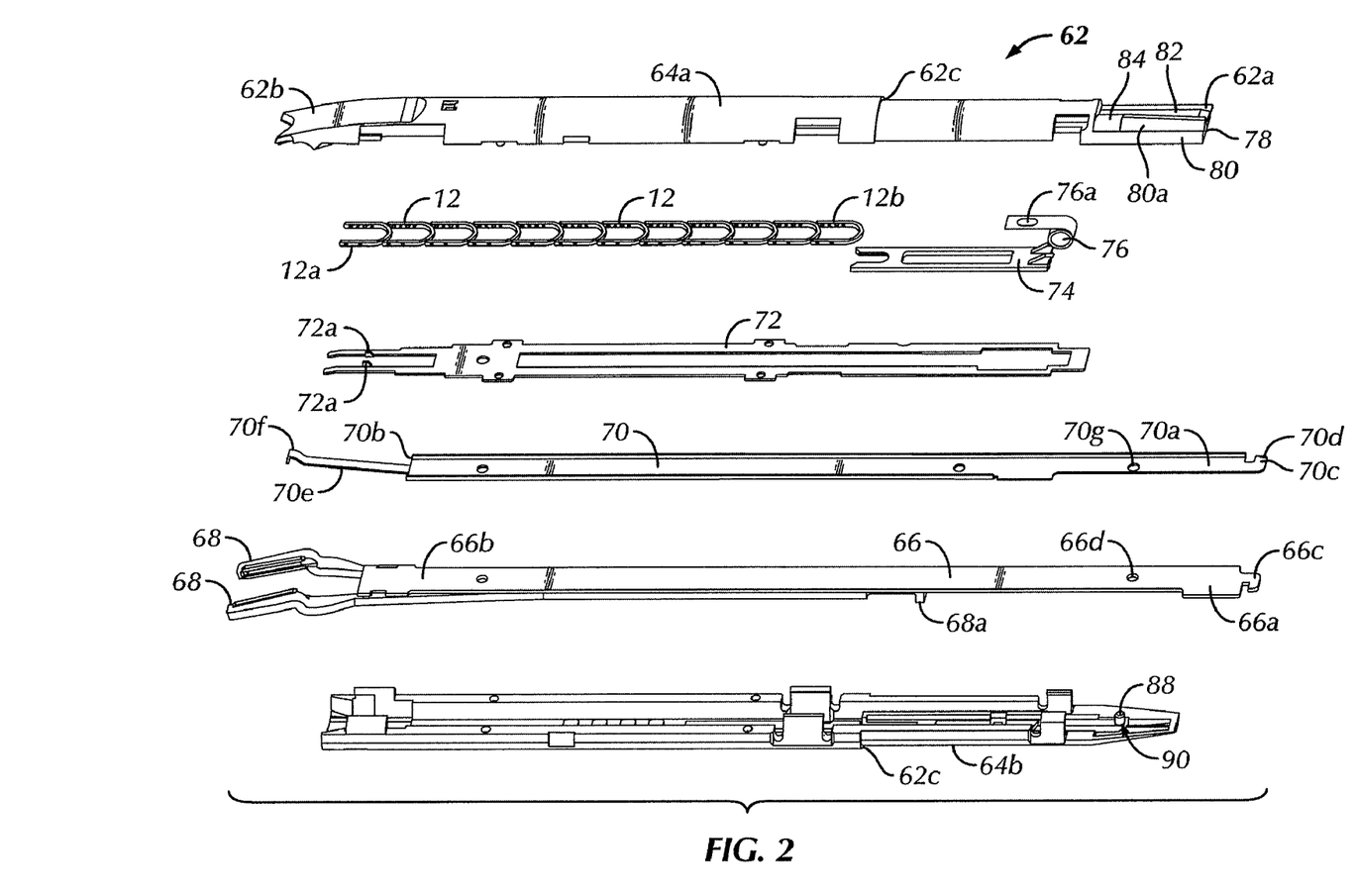
FIG. 2 is an exploded view of the cartridge shown in FIG. 1.

Referring to FIGS. 1, 2 and 3, the surgical clip applicator 10 includes a removeably mountable cartridge 62 that includes a plurality of the clips 12. The cartridge 62 has a proximal end 62a and a distal end 62b and preferably includes a housing 64 that is made up of an upper housing 64a and a lower housing 64b that are preferably snap fit or otherwise held together. The upper and lower housing 64a, 64b preferably contain a jaw driver 66 that is constructed of a thin, flat member that has a proximal end 66a and a distal end 66b. A first hook 66c extends from the proximal end 66a of the jaw driver 66. The distal end 66b of the jaw driver 66 is preferably slideable disposed over a pair of jaws 68 that at least partial extend from the distal end 66b of the jaw driver 66. The jaws 68 preferably join together at a proximal end 68a that extends downwardly into and preferably through the lower housing 64b. A clip driver 70 is preferably slideably provided on top of the jaw driver 66 and is preferably also a thin, flat member that has a proximal end 70a and a distal end 70b. A second hook 70c extends from the proximal end 70a of the clip driver 70 and preferably includes a bent corner 70d that is bent downwardly toward the jaw driver 66. A clip setter 70e preferably extends from the distal end 70b of the clip driver 70. The clip setter 70e preferably includes a hook 70f to engage with and set the next awaiting clip 12a. A plate 72 is preferably disposed over the clip driver 70 and is stationary with respect to the clip housing 64. The plate 72 preferably includes at least one and preferably two stops 72a to hold the next awaiting clip 12a stationary with respect to the clip housing 64 until the clip setter 70e urges the clip 12 over the stops 72a. The clips are preferably slideably provided on top of the plate 72. The next awaiting clip 12a abuts the stops 72a and the last clip 12b abuts a pusher 74. The pusher 74 is preferably spring biased from the upper housing 64a by a fourth spring member 76. The fourth spring member 76 is preferably a sheet spring that has a mounting hole 76a that is pinned or otherwise mounted to the upper housing 64a proximate the distal end 62b of the cartridge 62. The fourth spring member 76 urges the pusher 74 against the last clip 12b to constantly urge the next awaiting clip 12a against the stops 72a much like a paper stapler.

The lower housing 64b includes a releasable alignment mechanism or member 90 that is preferably in the form of an upwardly extending boss or projection 88 that extends through a first hole 66d in the jaw driver 66 and a second hole 70g in the clip driver 70. The projection 88 is preferably integrally molded with the lower housing 64b but the alignment member 90 may be separately formed and mounted to the upper and/or lower housing 64a, 64b. The projection 88 preferably extends through the first and second holes 66d, 70g to retain the clip driver 70 and jaw driver 66 in place relative to the cartridge housing 64 during storage, shipping and mounting such that the first and second hooks 66c, 70c remain in the proper position and alignment prior to connection with the ram housing 14.

Referring to FIG. 3, the lower housing 64b preferably includes an elongated longitudinal groove 64c extending from the proximal end 62a of the cartridge 62 to a circumferentially extending ledge 62c. A circumferential groove 64d extends partially around the cartridge 62 from the longitudinal groove 64c to a snap fit catch (not visible) between where the proximal end 68b of the jaws 68 extend through the lower housing 64b and the ledge 62c. The longitudinal groove 64c and the circumferential groove 64d preferably have a shape corresponding to the shape of the projection 14c on the distal end of the ram housing 14. The cartridge housing 64, the pusher 74 and the alignment member 90 are preferably constructed of polymeric materials and the clip and jaw drivers 66, 70, the jaws 68, the plate 72, the clips 12 and the fourth spring member 76 are constructed of metal though all of the components of the cartridge 62 may be made of any suitable material.

Referring to FIGS. 2 and 4D, the upper housing 64a toward the proximal end 62a of the cartridge 62 includes an end surface 78 that is at least partially perpendicular to the length of the cartridge 62 and is offset to one lateral side of the upper housing 64a. An arcuately shaped section 80 extends distally from the end surface 78 and has a partially indented surface 80a. A recessed area 82 is proximate the indented surface 80a and is generally parallel to the center of the upper housing 64a. The recessed area 82 extends downwardly (or inwardly toward the longitudinal center) more than the indented surface 80a. A ramp 84 extends from the recessed area 82 up to the partially indented surface 80a to bridge the recessed area 82 and the indented surface 80a.

Referring to FIG. 3, a new cartridge 62, or a cartridge containing clips 12 is removably mounted to the distal end 14b of the ram housing 14. During assembly, the longitudinal groove 64c and the projection 14c are aligned. The indicia 14e indicates where the longitudinal groove 64c is inserted and the longitudinal groove 64c and the projection 14c are preferably painted yellow or a similarly bright color (not shown) to highlight the required alignment between the cartridge 62 and the ram housing 14. Once the cartridge 62 is properly aligned with the ram housing 14, the proximal ends 66a, 70 of the jaw and clip drivers 66, 70 are inserted into the open distal end 14b of the ram housing 14 until the projection 14c engages with the longitudinal groove 64c.

Referring to FIGS. 4A and 4B, the projection 14c (FIG. 3) slides along the longitudinal groove 64c as the cartridge 62 is inserted further into the ram housing 14. Prior to the ledge 62c of the cartridge 62 engaging with the distal end 14b of the ram housing 14, the ram extension 32 contacts the end surface 78 of the cartridge 62 (FIG. 4B). Once the end surface 78 abuts the ram extension 32, further inserting of the cartridge 62 into the ram housing 14 urges the ram extension 32 toward the trigger housing 16. Though it is preferred that the ram extension 32 contacts the upper housing 64a of the cartridge 62, the ram extension 32 may initially abut against any surface or feature of the cartridge 62 that is capable of urging the ram extension 32 toward the trigger housing 16. Urging the ram extension 32 toward the trigger housing 16 causes the clip ram 24 to also slide back toward, and further into, the trigger housing 16. As a result, the rod 24d extends further into the trigger housing 16 and pivots the ram pivot 42 about the ram pivot axis 44. Once the ram pivot 42 has been sufficiently pivoted, the pivot extension 48 contacts the pawl 52, urging the pawl 52 downwardly to release the pawl 52 from the ratchet 50 (FIG. 4B). With the pawl 52 and ratchet 50 detached, the second spring member 40 is then able to pivot the trigger 36 about the trigger axis 38 and return the trigger 36 to an open position (shown in FIGS. 1, 4B and 4C) if the trigger 36 is not already in the open position, for example if the trigger 36 is in a partially closed position (FIG. 4A). Before insertion of the cartridge 62, the trigger 36 may have been left in the closed, or partially closed position upon removal of an empty cartridge (not shown) or the trigger 36 may be been inadvertently bumped or moved out of the open position during storage or between uses. Insertion of the cartridge 62 in this manner ensures that the trigger 36 is set to the open position and the jaw and clip rams 26, 24 are properly aligned before engaging the jaw and clip drivers 66, 70 with the jaw and clip rams 26, 24 respectively. Though it is preferred that the retaining member 86 be in the form of a ratchet 50 and pawl 52, the retaining member 86 may be any mechanism or member that releasably holds the trigger 36 in place with respect to the trigger housing 16 and is capable of being released by the action of installing the cartridge 62.

Referring to FIGS. 3 and 4C, once the trigger 36 has been set to the open position, the cartridge 62 is either fully inserted into the ram housing 14 or the cartridge 62 continues to slide into the ram housing 14 until the distal end 14b of the ram housing 14 abuts against the ledge 62c (FIG. 4). The ledge 62c preferably extends around the entire outer periphery of the cartridge 62 but the ledge 62c may have any shape or size that prevents the cartridge from being over inserted into the ram housing 14. Once the ledge 62c of the cartridge 62 abuts against the distal end 14b of the ram housing 14, the cartridge is twisted relative to the ram housing 14 in a fully assembled position (FIGS. 1, 4C) such that the projection 14c travels along the circumferential groove 64d. In the fully assembled position, the projection 14c is preferably proximal to and engaged with the proximal end 68b of the jaws 68 and the proximal end 68b of the jaws 68 extends into or through the opening 14d in the distal end 14b of the ram housing 14. A predetermined amount of force is required to both twist the cartridge into and out of the fully assembled position.

Referring to FIGS. 4C and 4D, twisting the cartridge 62 into the fully assembled position also causes the ram extension 32 to slide off or out of engagement with the end surface 78 and in alignment with the recessed surface 82. Because the clip ram 24 is spring biased from the jaw ram 26, the first spring member 28 rapidly extends the clip ram 24 and the ram extension 32 toward the distal end 14b of the ram housing 14. In the fully assembled position, the ram extension 32 extends over the recessed surface 82 and the ram pivot 42 pivots distally to release the pivot extension 48 from the pawl 52 and reengage the pawl 52 with the ratchet 50. Further, twisting the cartridge 62 into the fully assembled position releasably engages the first hook 66c of the jaw driver 66 with the second catch 26c such that movement of the jaw ram 26 moves the jaw driver 66. The second hook 70c also releasably engages with the first catch 24c such that movement of the clip ram 24 moves the clip driver 70. The bent corner 70d of the second hook 70c allows for the first catch 24c to ride up over the bent corner 70d and into engagement because as the first catch 24c is rapidly extending forward upon twisting of the cartridge 62 relative to the ram housing 14 it may abut against the second hook 70c before the second hook 70c and the first catch 24c are properly engaged.

Referring to FIGS. 2, 4C and 4D, once the cartridge 62 is in the fully assembled position, the surgical clip applicator 10 is ready for use. The user grasps the trigger housing 16 and places at least one finger in the trigger handle 36a. The user then squeezes the trigger handle 36a out of the open position toward the trigger housing 16. The trigger 36 pivots about the trigger axis 38 to urge the jaw ram 26 toward the distal end 14b of the ram housing 14. Simultaneously, the clip ram 24 is urged in the opposite direction of the jaw ram 26. As the user continues to squeeze the trigger 36 closer to the trigger housing 16 the clip and jaw rams 24, 26 urge the clip and jaw drivers 70, 66 respectively in opposite directions. The initial movement of the clip and jaw drivers 70, 66 disengages or releases the alignment member 90. Preferably, a predetermined amount of force shears or breaks the projection 88 away from the lower housing 64b to set the cartridge 62 from the storage or mounting position into an active position. The broken projection 88 preferably falls from the first and second holes 66d, 70g or is otherwise released from the clip and jaw drivers 70, 66 such that the clip and jaw drivers 70, 66 may slide relative to each other and to the housing 64. Though it is preferred that the alignment member 90 be in the form of a break away projection 88, the alignment member 90 may be any mechanism or member that keeps the clip driver 70 and the jaw driver 66 stationary with respect to the cartridge housing 64 in a storage, pre-mounted and mounting positions and releases the clip driver 70 and the jaw driver 66 with respect to each other and the cartridge housing 64 in the active position. For example, the alignment member 90 may be in the form of a boss or projection extending from a cantilever arm (not shown) that is pivoted and pulled from the first and second holes 66d, 70g when the cartridge 62 is in the fully assembled position.

As the trigger 36 is squeezed toward the trigger housing 16, the trigger 32 pivots against the ram pivot 42 and the rod 24d is urged back further in the trigger housing 16 such that the clip ram 24 pulls or urges the clip driver 70 back toward the trigger housing 16. As a result, the hook 70f is brought back toward the trigger housing 16 and is set in engagement with the proximal end of the next available clip 12a. As the hook 70f is pulled toward the trigger housing 16, the jaw ram 26 urges the jaw driver 66 toward the distal end 62b of the cartridge. The jaw driver 66 slides up the jaws 68 to begin to bring the jaws 68 closer together and pinch the jaws 68 closed. The trigger 32 is then set back into the open position as described below and because the clip ram 24 is spring biased to the jaw ram 26, the clip ram 24 is pulled distally toward the distal end 14b of the ram housing 14. As the clip ram 24 slides distally, the hook 70f urges the next available clip 12a toward to the distal end 62b of the cartridge 62 and over the stops 72a. The clip ram 24 continues to urge the clip 12a toward the distal end 62b of the cartridge until the clip 12 is placed between the jaws 68. The remaining clips 12 are advanced toward the distal end 62b of the cartridge 62 by the pusher 74 such that the next clip 12 abuts against the stops 72a. The first stroke or cycle of the trigger 36 preferably does not dispense a clip 12 and is used to release the alignment member 90 and set the next available clip 12a between the jaws 68. However, the initial trigger cycle, closing and then opening the trigger 36, may dispense a clip 12 and release the alignment member 90.

Once the alignment member 90 has been released, the next available clip 12a has been placed between the jaws 68 and the trigger 32 has been reset to the open position, the clip applicator 10 is ready for operation. The jaws 68 are placed within the patient such that the clip 12 straddles the desired tissue and/or device to be clipped. As the trigger 36 is squeezed toward the trigger housing 16, the trigger 32 pivots against the ram pivot 42 such that the clip ram 24 pulls the clip driver 70 toward the trigger housing 16 and the hook 70f is retracted from the clip 12 between the jaws 68 and the hook 70f is engaged with the available next clip 12a behind the stops 72a. As the hook 70f is pulled toward the trigger housing 16, the jaw ram 26 urges the jaw driver 66 toward the distal end 62b of the cartridge. The jaw driver 66 slides up the jaws 68 and begins to bring the jaws 68 closer together. As a result, the jaw 68 begin to pinch the clip 12 closed.

Referring to FIG. 4C, once the clip 12 is partially closed (not shown) between the jaws 68, the bosses 54 contact the arms 56a of the toggle 56. The toggle 56 is then pivoted proximally until the release bar 56b is pushed against and over (not shown) the ridge 52a of the pawl 52 to disengage the pawl 52 and the ratchet 50. Once the pawl 52 and ratchet 50 are disengaged, the clip 12 is at least partially closed. At this point the jaws 68 may be released to release a partially closed clip 12 or the trigger 36 may be squeezed further toward the trigger housing 16 to fully close or pinch together the clip 12. When the surgical clip applicator 10, for example, is used to perform a cholangiogram with a cholangiogram catheter (not shown), the catheter is inserted into a cystic duct (not shown) and the clip 12 is formed over the duct and catheter to hold the catheter in place relative to the duct. Fully closing the clip 12 would crush the catheter. A fully closed clip 12 or a substantially closed clip 12 however, may be desirable in other procedures such as pinching together human tissue (not shown). The closed position (shown in phantom in FIG. 1) is generally used to refer to the trigger 36 being in a position anywhere between forming a partially closed clip 12 to a fully closed clip 12.

The release bar 56b of the toggle 56 is retained on the ridge 52a in the closed position to keep the pawl 52 and ratchet 50 disengaged until the trigger 36 is released and pivoted by the second spring member 40 about the pivot axis 38 to the open position. Just prior to the trigger 36 entering the open position, an enlarged end 50b of the ratchet 50 contacts the arms 56a and pivots the toggle 56 distally to pull the release bar 56b over the ridge 52a and thereby re-engaging the pawl 52 with the ratchet 50. Rotation of the trigger 36 into the open position pulls the jaw ram 26 back toward the trigger housing 16 and releases the ram pivot 42 such that the jaw driver 66 is pulled back to fully open the jaws 68. At the same time, rotation of the trigger 36 into the open position moves the trigger 36 distally from the ram pivot 42 such that the first spring member 68 is able to pull the clip driver 70 toward the distal end 14b of the ram housing 14 and the set the next available clip 12a over the stops 72a and between the jaws 68. The clip driver 70 and the jaw driver 66 are now reset in a position to install another clip 12. Once all of the clips 12 have been exhausted from the cartridge 62, the clip driver 70 preferably urges the pusher 74 between the jaws 68 to jam the jaws 68 in an open position and prevents the jaws 68 from being closed. Jamming the jaws 68 indicates to the user that the cartridge 62 needs to be replaced and keeps the jaw and clip drivers 66, 70 in the mounting position such that the cartridge 62 may be disengaged from the ram 22 with the trigger 32 in the open or nearly open position.

Referring to FIGS. 4C and 4D, to remove the cartridge 62 from the ram housing 14, the cartridge 62 is twisted relative to the ram housing 14 in the opposite direction that the cartridge 62 was twisted relative to the ram housing 14 during mounting of the cartridge 62 to the ram housing 14. Twisting the cartridge 62 relative to the ram housing 14 disengages the clip driver 70 from the clip ram 24 and disengages the jaw driver 66 from the jaw ram 26. Additionally, twisting the cartridge 62 relative to the ram housing 14 urges the ram extension 32 against the ramp 84 which flexes the ram extension 32 outwardly and up onto the indented surface 80a on the arcuate surface 80. The cartridge 62 may then be pulled distally out of the ram housing 14 and discarded. A new cartridge 62 may then be mounted to the distal end 14b of the ram housing 14.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

We claim:

1. A surgical clip applicator adapted for the application of a surgical clip within the human body, the surgical clip applicator comprising:

a ram;

a ram housing having proximal and distal ends and at least partially surrounding the ram;

a trigger housing including a trigger having an open position and a closed position, the trigger housing being mounted to the proximal end of the ram housing, the ram extending partially into the trigger housing and operatively connected to the trigger, the trigger spaced a first distance from the trigger housing in the open position and spaced a second distance from the trigger housing in the closed position, the first distance being larger than the second distance, a retaining mechanism retaining the trigger with respect to the trigger housing between the open and closed positions;

a cartridge removably mounted into the distal end of the ram housing, the cartridge including a plurality of surgical clips, wherein mounting the cartridge into the distal end of the ram housing urges at least a portion of the ram into the trigger housing set the trigger in the open position.

2. A surgical clip applicator adapted for the application of a surgical clip to body tissue, the surgical clip applicator comprising:

a ram;

an elongated ram housing having proximal and distal ends and at least partially enclosing the ram;

a trigger housing including a trigger having an open position and a closed position, the trigger housing being mounted to the proximal end of the ram housing, the ram extending partially into the trigger housing and operatively connected to the trigger, the trigger spaced a first distance from the trigger housing in the open position and spaced a second distance from the trigger housing in the closed position, the first distance being larger than the second distance, the trigger urging the ram toward the distal end of the ram housing as the trigger is moved from the open position to the closed position, a retaining mechanism retaining the trigger with respect to the trigger housing between the open and closed positions;

a cartridge removably mounting into the distal end of the ram housing, the cartridge including a plurality of surgical clips and a pair of opposed jaws extending from a distal end of the cartridge, a clip driver for advancing one of the plurality of surgical clips at a time into the jaws when urged toward the distal end of the cartridge by the ram and a jaw driver for closing the jaws to pinch the one surgical clip when the jaw driver is urged toward the distal end of the cartridge by the ram, wherein mounting the cartridge to the distal end of the ram housing urges at least a portion of the ram into the trigger housing to set the trigger in the open position.

3. The surgical clip applicator of claim 2, wherein the retaining mechanism includes a ratchet for retaining the trigger in a position between the open and closed positions.

4. The surgical clip applicator of claim 3, wherein the ratchet includes a plurality of ratchet teeth and a pawl pivotably mounted to and spring biased from the trigger housing.

5. The surgical clip applicator of claim 2 further comprising a ram lever pivotably mounted to the trigger housing and operably mounted to the ram, the ram lever releasing the retaining mechanism when the cartridge is mounted to the ram housing to set the trigger to the open position.

6. The surgical clip applicator of claim 5, wherein the release mechanism includes a ratchet and pawl and the ram lever includes a ram lever extension for contacting and releasing the pawl from the ratchet.

7. The surgical clip applicator of claim 2, wherein the ram includes a jaw ram for connecting to the jaw driver, and a clip ram for connecting to the clip driver and for setting the trigger in the open position during mounting of the cartridge to the ram housing.

8. The surgical clip applicator of claim 7, wherein the clip ram is spring biased to the jaw ram.

9. The surgical clip applicator of claim 2, wherein the ram includes a ram extension extending from a distal end of the ram and engaging with a proximal end of the cartridge to urge the ram toward the trigger housing during mounting of the cartridge into the ram housing to set the trigger in the open position.

10. The surgical clip applicator of claim 9, wherein the ram extension returns at least partially toward the distal end of the cartridge when the cartridge is twisted relative to the ram housing during mounting of the cartridge into the ram housing.

11. The surgical clip applicator of claim 9, wherein the ram housing includes an inwardly extending support in sliding contact with the ram extension.

12. The surgical clip applicator of claim 2, wherein the ram housing includes an inwardly extending projection and the cartridge includes a corresponding inwardly extending groove such that the cartridge can only be inserted into the ram housing in a predetermined orientation.

13. The surgical clip applicator of claim 12, wherein the groove extends longitudinally from a distal end of the cartridge and then extends circumferentially such that the cartridge can be twisted relative to the ram housing once the cartridge is inserted into the ram housing and a snap fit that releasably retains the cartridge within the ram housing, the twisting of the cartridge relative to the ram housing engages the clip and jaw drivers with the ram.

14. The surgical clip applicator of claim 2, wherein the distal end of the ram housing includes indicia for aligning the cartridge with the ram housing during mounting of the cartridge into the ram housing.

15. The surgical clip applicator of claim 2, wherein the cartridge includes an alignment member that releasably retains the clip driver and the jaw driver in a mounted position such that the clip driver and the jaw driver are stationary with respect to each other and releases the clip driver and jaw driver in an active position once the cartridge is mounted into the ram housing and the trigger is moved out of the open position.

16. A surgical clip cartridge for use with a surgical clip applicator adapted for the application of a surgical clip to body tissue, the surgical clip applicator having an elongated ram housing having proximal and distal ends and including a ram, a trigger housing mounted to the proximal end of the ram housing, the ram extending partially into the trigger housing and operatively connected to a trigger having an open position and a closed position, the trigger spaced a first distance from the trigger housing in the open position and spaced a second distance from the trigger housing in the closed position, the first distance being larger than the second distance, the trigger urging the ram toward the distal end of the ram housing as the trigger is moved from the open position in which the trigger is enabled to initiate the application of a clip to the closed position in which the clip has been applied, the cartridge removably mounted into the distal end of the ram housing, the cartridge comprising:

a cartridge housing;
a plurality of surgical clips;
a pair of opposed jaws extending from a distal end of the cartridge housing;
a clip driver disposed within the cartridge housing for advancing one of the plurality of surgical clips at a time into the jaws when urged by the ram; and
a jaw driver disposed within the cartridge housing for closing the jaws to pinch the one surgical clip when urged by the ram,
wherein a alignment member releasably retains the clip driver and the jaw driver in a mounted position such that the clip driver and the jaw driver are stationary with respect to each other and releases the clip driver and jaw driver in an active position once the cartridge is mounted into the ram housing and the trigger is moved out to the open position.

17. The surgical clip cartridge of claim 16, wherein the alignment member is an inwardly extending projection that extends from the cartridge housing through the clip and jaw drivers in the mounting position and breaks away from the cartridge housing in the active position.

18. The surgical clip cartridge of claim 17, wherein a predetermined amount of force is required to break away the projection.

19. The surgical clip cartridge of claim 17, wherein the projection is integrally formed with the cartridge housing.

20. The surgical clip cartridge of claim 17, wherein the projection is positioned toward the proximal end of the cartridge housing.

* * * * *